United States Patent [19]

Albright et al.

[11] Patent Number: 4,891,188

[45] Date of Patent: Jan. 2, 1990

[54] UNPLUMBED STERILIZER

[75] Inventors: Donald W. Albright, Rochester; Raymond J. Miller, Penfield, both of N.Y.

[73] Assignee: MDT Corporation, Rochester, N.Y.

[21] Appl. No.: 52,057

[22] Filed: May 21, 1987

[51] Int. Cl.$^4$ .............................................. G05D 9/00
[52] U.S. Cl. .................................... 422/114; 422/116; 422/26; 436/55
[58] Field of Search ................. 422/110, 112, 116, 26, 422/103, 114, 113, 115, 106; 436/55, 147, 148

[56] References Cited

U.S. PATENT DOCUMENTS

| | | | |
|---|---|---|---|
| 3,107,975 | 10/1963 | Linder | 422/298 X |
| 3,443,884 | 5/1969 | Linder | 422/298 |
| 3,450,487 | 6/1969 | Wallden | 422/298 X |
| 3,834,872 | 9/1974 | Joslyn | 422/299 X |

Primary Examiner—Barry S. Richman
Assistant Examiner—Lynn M. Kummert
Attorney, Agent, or Firm—Trask, Britt & Rossa

[57] ABSTRACT

An unplumbed sterilizer is provided with an exhaust valve means which allows automatic liquid introduction to the sterilizing chamber with the door closed even after a prior sterilization cycle has been run. The exhaust valve means also minimizes the possibility of trapping air within the chamber.

9 Claims, 1 Drawing Sheet

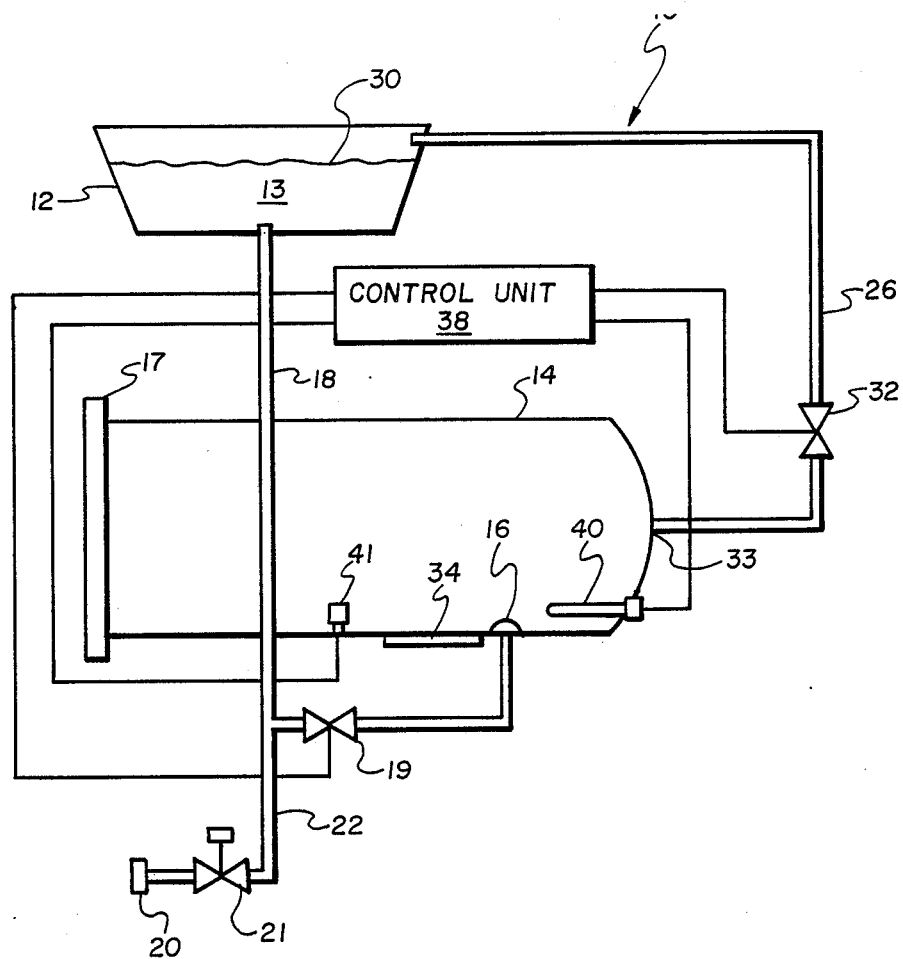

UNPLUMBED STERILIZER

BACKGROUND OF THE INVENTION

The present invention is directed to improved unplumbed sterilizers.

Unplumbed sterilizers are conventionally provided with a reservoir for holding a liquid such as water which is used to produce steam within the sterilization chamber. Typically, unplumbed sterilizers are relatively small units which are relatively simple in construction as compared to permanently fixed sterilizers which are hooked up to a steam supply line and drain. Typically, these unplumbed sterilizers rely upon a steam trap for releasing trapped air or steam from the chamber. A problem associated with such sterilizers is that they cannot be automatically charged with the correct amount of water for a subsequent sterilization cycle when the door is closed following the completion of a prior sterilization cycle. Another problem associated with this type of sterilizer is the trapping of air within the chamber after a sterilization cycle has been completed. Because of the hysteresis of the steam trap, the trap may not open or it may open for only a short period of time, thereby trapping air within the chamber. Because air is an insulator, the effectiveness of a steam sterilization cycle remains in question so long as air remains in the chamber.

The improved apparatus and method of operation of this invention overcome or minimize the aforementioned problems of previous unplumbed sterilizers.

The present invention comprises an improved construction and control mechanism for unplumbed sterilizers. The sterilizers of this invention include a sterilizing chamber with an associated liquid reservoir, as is typical of unplumbed sterilizers. The chamber has the usual access door and means for converting liquid to steam. Liquid is introduced from the reservoir to an inlet to the chamber through a first passageway, such as piping. A first control valve is associated with the first passageway and is operative selectively to open or close as needed to permit or prevent the flow of liquid through the chamber inlet. A second passageway, extends from an outlet from the chamber, and conducts steam from the chamber to a drain system, the atmosphere or back to the reservoir. A second control valve is associated with the second passageway and is operative selectively to open or close, thereby to permit or prevent the exhaust of air and/or steam through the outlet. An important aspect of this invention is the sequencing of the first and second control valves in coordination with the several steps of a sterilization cycle. Proper sequencing may be achieved in various ways, but as presently envisioned, electronic control means, including sensing and timing components, are provided for this purpose. The apparatus of this invention makes available methods of operation not previously practicable to realize with unplumbed sterilizers.

At the commencement of a sterilization cycle, a load is placed into the sterilizing chamber, the door of the chamber is closed, the heating element associated with the chamber is turned on. The first valve is turned on to permit liquid to enter the chamber. The liquid is converted to steam. The control means operates to hold the second valve open during the liquid introduction step. Significantly, the second valve is held open after the first valve is closed; that is, after the appropriate amount of liquid has been charged to the chamber. The second valve will be closed by operation of the control means in response to events signalled by sensors within the chamber or timing elements associated with the control means. In any event, the second valve is prevented from closing until it is certain that all of the air has been displaced from the chamber.

According to certain embodiments of the invention, the control means, which ideally includes a microprocessor in association with a temperature sensor, a timer, solenoids connected to drive the first and second valves, and other circuit components, effects a sequence of operation of both the first and second valves. The first and second valves are both opened at the commencement of a sterilization cycle. The first valve is closed after a prescribed time or in response to a level indicator. The second valve is closed after a second prescribed time interval or in response to an indication of temperature conditions in the chamber. Preferably, the second valve is closed a selected time interval following the sensing of a selected temperature within the chamber.

DESCRIPTION OF THE DRAWING

The FIGURE is a schematic diagram of a sterilizer made in accordance with the present invention.

DETAILED DESCRIPTION OF THE INVENTION

Referring to the drawing there is illustrated a schematic diagram of an unplumbed sterilizer 10 made in accordance with the present invention. For the purposes of this invention the term "unplumbed sterilizer" refers to a sterilizer which is not hooked up to any external steam source for the introduction of steam. Any steam required by sterilizer 10 will be produced by the unit itself. Sterilizer 10 is provided with a reservoir 12 for holding a quantity of a liquid 13 such as water. A sterilization chamber 14 is provided with an access door 17 and an inlet/outlet port 16. The inlet/outlet port 16 is connected to reservoir 12 by passageway 18 which acts as a conduit for passage of water from reservoir 12 into chamber 14. Valve 19 is provided in passageway 18 for opening and closing passageway 18. The inlet/outlet port 16 is also connected to a drain plug 20 by passageway 22. A manual valve 21 is provided for controlling flow through passageway 22 for draining the reservoir 12 or chamber 14 of water. In the particular embodiment illustrated a drain plug 20 is provided thereby making manual valve 21 optional.

A passageway 26 is provided between reservoir 12 and sterilization chamber 14 to permit exhaustion of air and/or steam from chamber 12 to atmosphere. Preferably the outlet 28 of passageway 26 is placed in the reservoir above water line 30. The outlet 33 of chamber 14 is connected to passageway 26 at any convenient point. An exhaust valve 32 is provided in passageway 26 so as to maintain passageway 26 either in the open or closed state. In the particular embodiment illustrates valves 32 and 19 are solenoid valves and are appropriately opened or closed by microprocessor control unit 38. The microprocessor control unit 38 is typical of control units used to control sterilizers of the prior art and may be programmed as desired by one of ordinary skill so as to provide the appropriate sterilization cycles. A heating element 34 is provided on chamber 14 for turning the water provided in chamber 14 therein into steam and for heating the steam to the desired temperature. In the particular embodiment illustrated heating element 34 is disposed on the outside of chamber 14, however, the heating element 34 may be placed inside chamber 14. The heating element 34 is also controlled by conrol unit 38. A temperature sensor 40 is provided within chamber 14 for monitoring the temperature within the chamber. An optional liquid level sensor 41 is provided in the embodiment illustrated to sense the proper water level thereby precisely controlling the closing of valve 19. The information sensed by sensor 41 is relayed to control unit 38 which operates to close valve 19 when the water level reaches a predetermined level.

In operation, the reservoir 12 is filled with an appropriate amount of water. An appropriate load to be sterilized is introduced into the chamber 14. The chamber is then sealed by closing access door 17. A predetermined amount of water is allowed to flow from the reservor 12 through passageway 18, valve 19 and port 16 into sterilization chamber 14. By determining the CV of the valve 19 and the approximate pressure head of the water at the chamber inlet/outlet port 16, one can accurately predict the amount of water which will be delivered to chamber 14 during a selected time period through which valve 19 is maintained open. Alternatively the amount of water allowed to enter chamber 14 can be determined by the control unit 38 in response to liquid level sensor 41. During the filling operation valve 32 is positively maintained open by control unit 38. Valve 32 has a CV rating (a standard flow coefficient used in the trade to describe flow rate characteristics) which allows free and easy passage of air and/or steam therethrough, preferably valve 32 has a CV of at least about 0.9, and in the particular embodiment illustrated has a value of about 0.96. Heating element 34 is then activated by control unit 38 to heat the water and convert it to steam to a preselected temperature. The steam is typically maintained at about 121° C. to 135° C. during the exposure phase of the sterilization cycle. During heating of the water to form steam, valve 32 is maintained open to allow air to freely escape until the steam within chamber 14 is at a predetermined temperature. Preferably valve 32 is not closed until the temperature of the environment in the chamber 14, as measured by temperature sensor 40, reaches a temperature of about 80° C. Applicants have found that when this temperature is reached substantially all of the air in the chamber will have been exhausted. The preselected temperature at which valve 32 is closed may vary depending upon the physical construction of the sterilizer. In any event, it is important that the steam produced displace substantially all of the air out of chamber 14.

An optional precautionary measure is made possible by the solenoid valve 32. The control unit 38 may be programmed so that a predetermined amount of time must pass after the preselected temperature is reached in the chamber 14 before valve 32 is closed. For example, valve 32 may be kept open for about an additonal minute following the sensing by sensor 40 of 80° C. before valve 32 is closed. The outlet 33 of chamber 14 to passageway 26 is preferably placed directly above the water line of a full charge of water. Since steam is lighter than air, this placement will enhance exhausting of the air out of the chamber 14. Steam traps of the prior art operate independently of the cycle operation of the sterilizer. Steam traps close at a specific temperature which is sensed by the trap itself. The operation of valve 32 just described avoids the problems inherent in a steam trap's closing prior to exhausting all of the air present in the chamber. This problem is particularly likely at the commencement of a cycle following a sterilization cycle which has recently been completed.

After the sterilizing chamber 14 has been filled and brought up to proper operating temperature, the sterilizer 10 goes through the exposure portion of the sterilization cycle as programmed by the operator. After the exposure phase of the sterilization cycle has been completed, the temperature and pressure in the chamber are lowered so that door 17 may be opened. The pressure in the chamber 14 may be lowered in a conventional manner or brought down as described in co-pending application Ser. No. 019,344, filed 2-26-87. The control unit 38 by appropriate electrical means opens valve 32 allowing steam to exit from the chamber 14 to atmosphere.

After chamber 14 has been brought back to its normal atmospheric pressure the door 17 is opened thereby allowing access to the sterilized load in chamber 14. Thereafter a second load may be immediately placed in the chamber 14 for running of another sterilization cycle. The door is again closed and water is allowed to enter the chamber 14. During initial entrance of the water into chamber 14 during this second sterilization cycle and any other succeeding sterilization cycles that are initiated soon after a cycle has been completed, there exists the possibility of water flashing off into steam due to the temperature of the chamber 14. When a steam trap is relied upon for venting, automatic introduction of water into the chamber with the door 17 closed is not feasible. In such cases the water must be introduced into the chamber 14 with the door open and manually by the operator. During such introduction of water the operator is exposed to the risk of contact by flashing steam. If water is allowed to flow into a sterilization chamber with its door closed, flashing of water into steam could occur due to residual heat in the chamber. The steam so produced would create pressure within the chamber if the steam trap used to vent the chamber is closed for example, by virtue of the previously described hysteresis effect imposed by a previous sterilization cycle. This presssure would affect the amount of water flowing into the chamber in a gravity fed system such as that illustrated. As shown, only the small pressure head of the water forces the water from reservoir 12 into the chamber 14. Because steam traps are characterized by a relatively low CV value, generally in the range of 0.03 to 0.46, a steam trap does not allow for adequate air to escape from the chamber prior to the trap's closing. However, with the solenoid valve 32 open an insignificant amount of pressure is built up within the chamber 14 even if flashing occurs during the initial introduction of water. Therefore, there is no possibility of producing back pressure which would inhibit the amount of water to flow within the chamber. Furthermore, valve 32 is positively controlled by control unit 38 assuring that it will be in the open or closed state as required. Sufficient water may be introduced into chamber 14 through valve 19 to allow for flashing losses through valve 32.

As previously discussed after an initial sterilization cycle has been run in a sterilizer there is no assurance that the steam trap is either open or closed; the hysteresis of the valve may hold the trap closed when it should be open for purposes of the next cycle. Air removal presents a significant problem when a second sterilization cycle is run soon after a previous cycle. By contrast, the present invention permits procedures whereby the valve 32 is positively controlled by the control unit 34 and is opened or closed in direct correspondence to the changing requirements of the sterilization cycle. Exhaust valve 32 is positively kept open both during the automatic filling cycle and/or the initial heating phase of the water in the chamber. Additionally applicants invention allows for automatic filling of the sterilizing chamber with the access door closed.

It is understood that various changes or modifications may be made without departing from the scope of the present invention. For example, but not by way of limitation, solenoid valves 19, 32 could be replaced with other valves having the appropriate CV ratings.

What is claimed is:

1. In an unplumbed sterilizer in which a sterilizing chamber is connected in fluid circuit with a reservoir through piping and a flow control device to effect repetitive cycles during which a load is introduced to the chamber, the chamber is sealed, liquid is introduced through an inlet to the chamber from the reservoir and is heated in the chamber to create steam, thereby to displace air from the chamber, the load is exposed to steam at elevated pressure and temperature, the steam is thereafter exhausted through an outlet from the chamber and the chamber is opened to remove the load, the improvement comprising: a temperature sensor positioned within said chamber; and control means in circuit with said temperature sensor, a first said flow control device operative to control the flow of liquid from said reservoir to said inlet, and a second said flow control device operative to control the passage of steam from said outlet;

said control means being operable to open both said first and second flow control devices during a first period until a predetermined quantity of liquid flows from said reservoir to said chamber, to thereafter close said first flow control device while holding said second flow control device open during an air exhaust period during which said liquid is converted to steam and thereafter to hold both said first and second flow control devices closed until the end of an exposure period.

2. An improvement according to claim 1 wherein said reservoir is physically positioned above said chamber, and fluid flow through said inlet is in response to gravity.

3. An improvement according to claim 1 wherein said first and second flow control devices are electrically controlled valves.

4. An improvement according to claim 3 wherein said control means comprises a microprocessor programmed in accordance with the requirements of a sterilization cycle to hold said second valve open until said temperature sensor detects a preselected temperature within said chamber.

5. An improvement according to claim 4 wherein said microprocessor includes a timer and is programmed to hold said second valve open for a predetermined time interval following the detection by said temperature sensor of said preselected temperature.

6. An improvement according to claim 3 wherein said control means is operable to open said first valve following the completion of said exposure period, thereby to permit the draining of liquid from said chamber through said inlet.

7. An improvement according to claim 6 wherein said control means is further operable to open said second valve after said first valve is opened upon the detection by said temperature sensor of a preselected temperature within said chamber lower than the temperature within the chamber during said exposure period, thereby permitting the exhaust of steam through said outlet.

8. An improvement according to claim 7 wherein said control means comprises a microprocessor programmed in accordance with the requirements of a sterilization cycle to hold said second valve open until said temperature sensor detects a preselected temperature within said chamber.

9. An improvement according to claim 8 wherein said microprocessor includes a timer and is programmed to hold said second valve open for a predetermined time interval following the detection by said temperature sensor of said preselected temperature.

* * * * *